United States Patent [19]

Ogawa et al.

[11] Patent Number: 4,947,245

[45] Date of Patent: Aug. 7, 1990

[54] IMAGE PICKING-UP AND PROCESSING APPARATUS

[75] Inventors: Ichirou Ogawa; Kouzou Yoshimura, both of Kanagawa; Kenzou Ueshima; Shinichi Nishimoto, both of Kyoto, all of Japan

[73] Assignees: Sumitomo Electric Industries, Ltd., Osaka; Kabushiki Kaisha Morita Seisakusho, Kyoto, both of Japan

[21] Appl. No.: 354,993

[22] Filed: May 22, 1989

[30] Foreign Application Priority Data

May 23, 1988 [JP] Japan ................................ 63-125312
Jul. 19, 1988 [JP] Japan ................................ 63-180860

[51] Int. Cl.$^5$ ............................................. A61B 1/04
[52] U.S. Cl. ............................................ 358/98; 128/6
[58] Field of Search ................................ 358/98; 128/6

[56] References Cited

U.S. PATENT DOCUMENTS

| | | | |
|---|---|---|---|
| 4,168,882 | 9/1979 | Hopkins | 350/573 |
| 4,413,278 | 11/1983 | Feinbloom | 358/98 |
| 4,539,586 | 9/1985 | Danna | 358/98 |
| 4,601,284 | 7/1986 | Arakawa | 358/98 |
| 4,639,772 | 1/1987 | Sluyter et al. | 358/98 |
| 4,754,328 | 6/1988 | Barath | 358/98 |
| 4,860,094 | 8/1989 | Hibino | 358/98 |

FOREIGN PATENT DOCUMENTS

| | | |
|---|---|---|
| 2563934 | 11/1985 | France . |
| 2591094 | 6/1987 | France . |
| 61-190518 | 11/1986 | Japan . |
| 63-267329 | 11/1988 | Japan . |
| 8502101 | 5/1985 | World Int. Prop. O. . |
| 8807694 | 10/1988 | World Int. Prop. O. . |

*Primary Examiner*—Howard W. Britton
*Attorney, Agent, or Firm*—Cushman, Darby & Cushman

[57] ABSTRACT

An image picking-up and processing apparatus particularly suitable for use in dental treatment comprises a transmission and conversion section including an image sensor for detecting input light from an object, an objective lens, and a light guide for transmitting illumination light; a control section including a control unit for producing an image signal on the basis of an output signal from the image sensor, and a light source for emitting the illumination light; and an interchangeable image processing section detachably connected to the transmission and conversion section for processing the image signal to reproduce image information in a desired form. An interchangeable image picking-up section, for example, an endoscope including an objective lens, an image fiber for transmitting the input light, and a light guide for transmitting the illumination light is detachably connected to the transmission and conversion section.

20 Claims, 14 Drawing Sheets

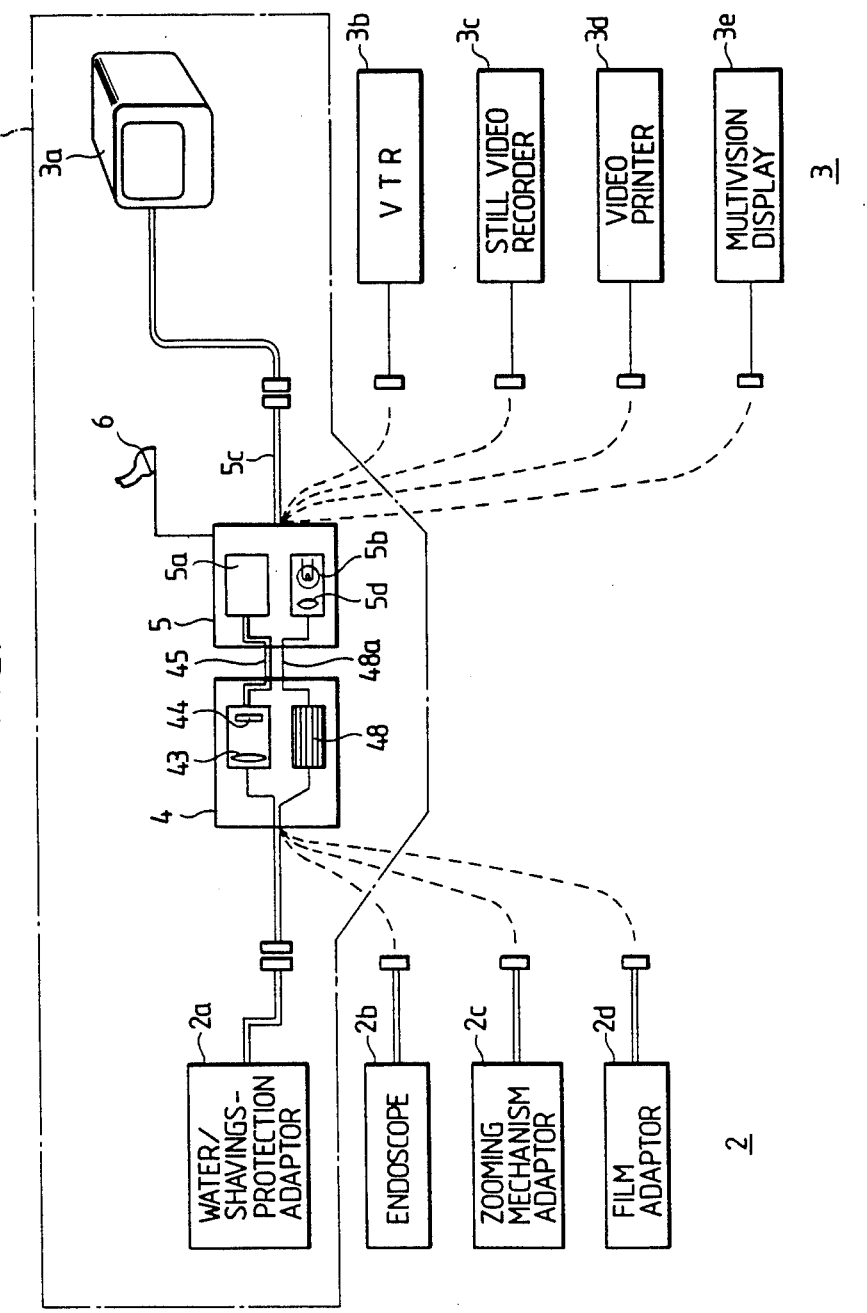

ENDOSCOPE | TRANSMISSION AND CONVERSION SEC.

← ENDOSCOPE | TRANSMISSION AND CONVERSION SEC. →

OBSERVING DIRECTION

VIEW RANGE

OBSERVING DIRECTION

IMAGE PICKING-UP AND PROCESSING APPARATUS

BACKGROUND OF THE INVENTION

The present invention relates to an image pickingup and processing apparatus and, more particularly, relates to an image picking-up and processing apparatus suitable for dental treatment, diagnosis and the like.

Heretofore, as an oral cavity observing apparatus for use in dental treatment for bad teeth, periodontal diseases and the like, there known is an apparatus of the type which includes a video camera, a television set connected to the video camera, and an illumination light guide attached to the outside of the video camera to guide light to thereby illuminate an object to be observed, so that an image picked up by the video camera is observed through the television set. Just an oral cavity and the external appearance of teeth can be observed by the apparatus of this type. In other words, nothing but information of teeth visible from the outside can be recorded or observed by the apparatus of this type. Therefore, there has been proposed an apparatus in which an endoscope is attached to a front end of the video camera of the above-mentioned apparatus to make it possible to record or observe the inside of a root canal (e.g., Japanese Utility Model Application Unexamined Publication No. 190518/1986).

The aforementioned conventional apparatus cannot observe both the inside of an oral cavity and the inside of a root canal. This is due to the following reasons. In order to make a root canal endoscope also act as an oral cavity endoscope a plurality of lenses are required, because the root canal endoscope and the oral cavity endoscope are different in the focal length of an objective lens for focusing an object image on the image sensor. In the case where these lenses and mechanisms for adjusting their optical axes and focuses are incorporated in the endoscope, the size of the endoscope is increased and the handling property is deteriorated. Furthermore, the observation of the inside of a root canal and the observation of the inside of an oral cavity are extremely different in the required illuminance because an oral cavity is very wider than a root canal. If the illumination for observation of a root canal is used for observation of an oral cavity, the obtained image is deteriorated because of the shortage of illuminance. If the illumination for observation of an oral cavity is used for observation of a root canal, the obtained image is also deteriorated because of the excess of illuminance.

However, both observations of the inside of an oral cavity and the inside of a root canal are necessary for suitable progression of dental treatment. For this reason, it was necessary for dentists to buy a plurality of apparatuses, necessitating a large fund.

Further, in the conventional observing apparatus, the image of the inside of an oral cavity or root canal can be merely observed or recorded, and it is impossible to observe detailed parts and to campare at a glance the changes in diseased parts.

SUMMARY OF THE INVENTION

It is therefore an object of the present invention to provide a low-cost image picking-up and processing apparatus capable of observing various objects, particularly the inside of an oral cavity and the inside of a root canal to thereby solve the aforementioned problems.

The image processing apparatus according to the present invention comprises: a transmission and conversion section including an image sensor for detecting input image information, and a first light guide for transmitting illumination light; an image picking-up section removably attached to a front end of the transmission and conversion section, for transmitting the input image information to the transmission and conversion section; a control section connected to the transmission and conversion section through a signal cable and a second light guide, including a control unit for controlling the image sensor and producing an image signal on the basis of an output signal from the image sensor and a light source for emitting the illumination light, the illumination light emitted from the light source being transmitted to a rear end of the first light guide through the second light guide; and an image processing section removably connected to the control section, for processing the image signal to reproduce image information in a desired form.

The image processing apparatus according to the present invention is provided with various interchangeable image picking-up means corresponding to various objects of observation, which are detachably connected to the transmission and conversion section. A picked-up image is converted into an electric signal by the transmission and conversion section and the image of the object is processed on the basis of the electric signal. Accordingly, various types of observations can be carried out by a single apparatus.

Other and further objects features and advantages of the invention will appear more fully from the following description taken in connection with the accompanying drawings.

BRIEF DESCRIPTION OF THE DRAWINGS

FIG. 1 is a schematic view showing the construction of an image processing apparatus according to the present invention;

DETAILED DESCRIPTION OF THE PREFERRED EMBODIMENTS

Figure 2A:
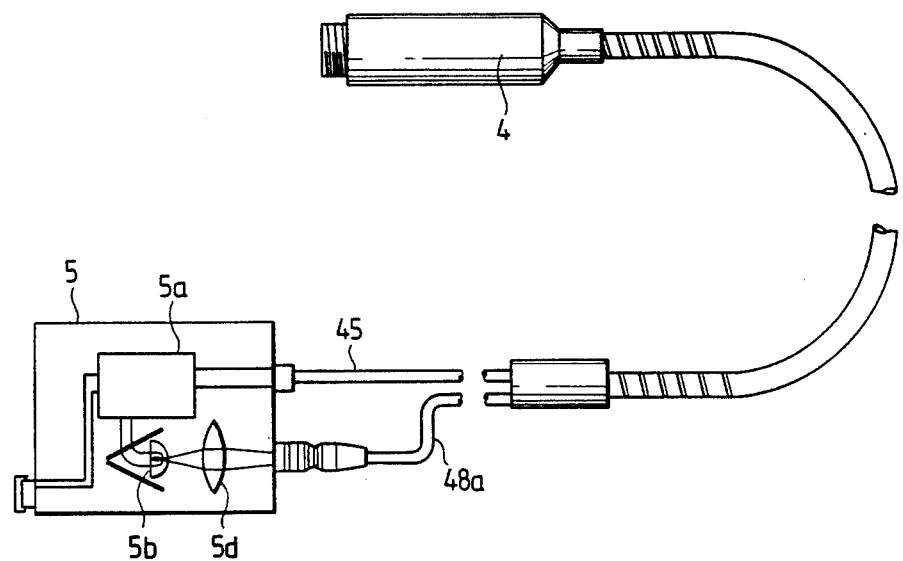
FIGS. 2(a) to 2(d) are views showing the specific structure of the transmission and conversion section of the image processing apparatus depicted in FIG. 1.

Referring to the drawings, embodiments of the present invention will be described hereunder.

In the drawings, like parts represented by the same reference numerals have the same functions, and accordingly, duplication of description thereof will be avoided.

FIG. 1 is a schematic diagram showing the construction of an image picking-up and processing apparatus as an embodiment according to the present invention.

As shown in FIG. 1, the image picking-up and processing apparatus 10 has an image picking-up section 2 such as an oral cavity endoscope 2b, and a transmission and conversion section 4. The transmission and conversion section 4 and the image picking-up section 2 are removably attached to each other. By interchanging the image picking-up sections 2 to be attached to the transmission and conversion section 4, image information of various objects such as the inside of an oral cavity, the inside of a root canal, an X-ray film can be picked up. Examples of the image picking-up section 2 include a water/shavings-protection adaptor 2a capable of protecting parts such as an objective lens inside the transmission and conversion section 4, an endoscope 2b, a zooming mechanism 2c capable of scaling up and down the image, and a film adaptor 2d for holding a film such as an X-ray film. The transmission and conversion section 4 includes an image sensor 44 such as CCD for converting the image information picked up by the image picking-up section 2 into an electric signal, an objective lens 43 for focusing an image on the image sensor 44, and a light guide 48 for transmitting illumination light to the image picking-up. section 2.

Further, the image picking-up and processing apparatus has a control section 5 connected to the transmission and conversion section 4 through a signal cable 45 and a light guide 48a, and an image processing section 3 interchangeably attached to the control section 5. The signal cable 45 and the light guide 48a are combined and put into a tube. The control section 5 includes a control unit 5a for controlling the image sensor 44 of the transmission and conversion section 4 and producing an image signal on the basis of an output signal from the image sensor 44, and a light source 5b for supplying illumination light. The control unit 5a is connected to the image sensor 44 through the signal cable 45. Light emitted from the light source 5b is guided to a rear end surface of the light guide 48 through the light guide 48a. Further, an operation switch 6 is connected to the control unit 5. It is preferable that the operation switch 6 is in the form of a foot switch which can be operated by foot to make operator's, for example dentist's, hand free.

The image picking-up and processing apparatus has an image processing section 3 such as a monitor television set 3a interchangeably connected to the control section 5. The image processing section 3 is connected to the control section 5 through a signal line 5c. Examples of the image processing section 3 include a monitor television set 3a used as an image display; a VTR 3b and a still video recorder 3c respectively used as an image recorder; a video printer 3d used as an image printer; and a multivision display 3e used as an image-division display. By interchanging these image processing devices, picked-up images can be easily observed and compared with each other.

In the following, the aforementioned constituent sections are described in detail.

ARRANGEMENT OF TRANSMISSION AND CONVERSION SECTION AND CONTROL SECTION

The arrangement of the transmission and conversion section 4 and the control section 5 connected to each other is shown in FIG. 2(a). As shown in FIG. 2(a), the transmission and conversion section 4 and the control section 5 are separately arranged and connected to each other through a signal cable 45 and a light guide 48a. The signal cable 45 and the light guide 48a are combined at the side of the transmission and conversion section 4, and are branched into two parts at the side of the control section 5 so as to be connected to connection terminals of the control section 5 through a signal cable connector and a light guide connector, respectively. In general, the control section 5 is fixed and the transmission and conversion section 4 is carried by a dentist's hand.

TRANSMISSION AND CONVERSION SECTION

The transmission and conversion section 4 has an objective lens 43 for focusing an image picked up by the image picking-up section 2 onto the image sensor 44, and an illumination light guide 48 for guiding light from the control section 5 to illuminate an object of observation.

Figure 2B:
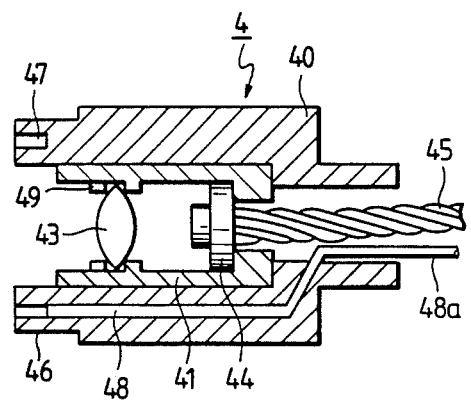
Figure 2C:
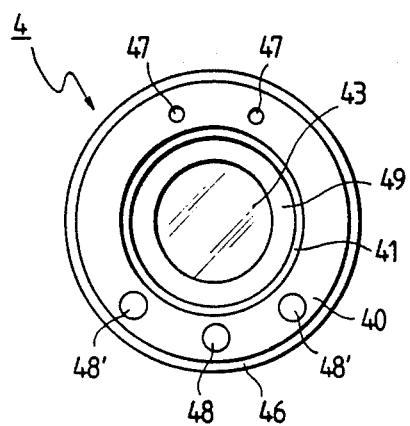

The first structure of the transmission and conversion section 4 is shown in a sectional view of FIG. 2(b) and a side view of FIG. 2(c). The first structure comprises a substantially cylindrical body 40 having an open front end, a holder 41 embedded in the body 40, an objective lens 43 provide in the holder 41, and an image sensor 44. The image sensor 44 is placed on the same optical axis as the objective lens 43 and in a focus plane of the objective lens 43.

Figure 2D:
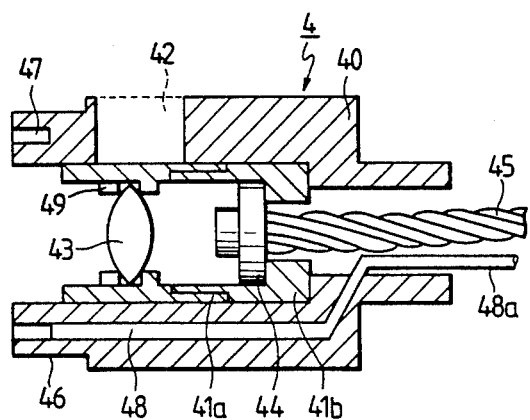

The second structure of the transmission and conversion section 4 is shown in a sectional view of FIG. 2(d) and a sidet view of FIG. 2(c), the latter being common to the first structure. The second structure comprises a substantially cylindrical body 40 having an open front end and. an opening 42 provided in a circumferential wall thereof, a lens holder 41a and a sensor holder 41b both embedded in the body 40, an objective lens 43 provided in the lens holder 41a, and an image sensor 44 provided in the sensor holder 41b. While the objective lens 43 is placed on the same axis as the image sensor 44, the lens holder 41a is adapted to move back and forth so that an image of the object can be focused on the image sensor 44 in accordance with a distance between the object and the objective lens 43. The lens holder 41a and the sensor holder 41b are threadedly engaged with each other, and the back-and-forth movement of the lens holder 41a is effected by rotating itself by hand through the opening 42.

The image sensor 44 may be constituted by a photoelectric conversion device such as a solid state image sensor (inclusive of CCD), by which the image formed by the objective lens 43 is photoelectrically converted. A resultant electric signal is transmitted to the control section 5 through the cable 45. The objective lens 43 is fixed within the holder 41 or lens holder 41a by a lens stopper 49.

The image picking-up section 2 is designed to be removably attached to a front end of the transmission and conversion section 4. That is, a male screw 46, which is to be engaged with a female screw formed in the image picking-up section 2, is formed in a front end portion of the body 40. Further, positioning holes 47, into which positioning pins formed on the image picking-up section 2 are respectively inserted, are formed in predetermined positions of the front end portion of the body 40. Further, a light guide 48 is inserted through the body 40 of the transmission and conversion section 4 along the axis direction. An end of the light guide 48 reaches the front end surface of the body 40 so that the illumination light can be emitted therefrom.

Since the front end of the body 40 having the objective lens 43 and the light guide 48 therein is opened, the transmission and conversion section 4 can singly act as an oral cavity endoscope. An image of the inside of an oral cavity illuminated with light emitted from the light guide 48 is focused on the image sensor 44 by the objective lens 43. The output electric signal from the image sensor 44 is transmitted to the control section 5 through the cable 45. The transmitted electric signal is processed in the control section 5 and further transmitted to the image processing section 3. Thus the image of the oral cavity can be observed as a picture image displayed on the monitor television set 3a, etc.

The image sensor 44 is housed in a double pipe structure formed by the body 40 and the holder 41 (or lens holder 41a and sensor holder 41b) to perfectly block leakage light, so that the image sensor 44 can detect the image only through the reflected light from the object.

CONTROL SECTION

As shown in FIG. 2(a), the control section 5 includes a light source 5b for emitting light to illuminate the object of observation, and a lens 5d provided in front of the light source 5b for converging light emitted therefrom to an incident end surface of the light guide 48a. The control unit 5a processes the electric signal from the image sensor 44 and send it to the image processing section 3. In addition, a foot switch 6 for controlling the image processing section 3, the light source 5b, etc. is connected to the control section 5.

WATER/SHAVINGS-PROTECTION ADAPTOR

During the observation of the inside of an oral cavity, water for cleaning the oral cavity may be scattered to invade the transmission and conversion section 4. In particular, in the observation with concurrent use of a tooth-cutting drill, tooth shavings may be scattered to damage the objective lens 43 and other parts. To solve this problem, a water/shavings-protection adaptor as shown in FIG. 2(b) is preferably attached to the transmission and conversion section 4.

Figure 3A:
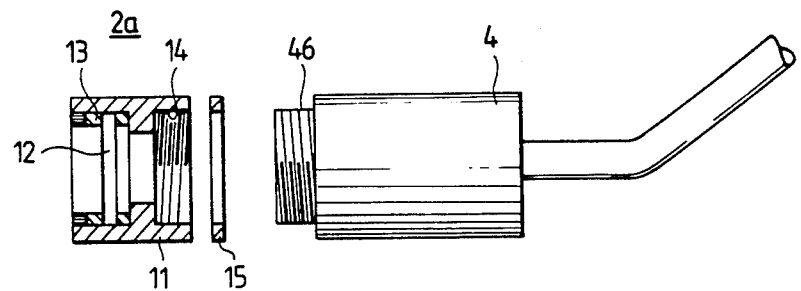
FIGS. 3(a) and 3(b) are views showing the structure of the water/shavings-protection adaptor depicted in FIG. 1.

The structure of the water/shavings-protection adaptor 2a is shown in FIG. 3(a). The water/shavings-protection adaptor 2a has a substantially cylindrical body 11 and a transparent plate 12 formed of glass or the like. A female screw 14, which is to be engaged with the male screw 46 formed in the transmission and conversion section 4, is formed in the inner surface of a rear end of the body 11. The transparent plate 12 is arranged within the body 11 so as to be perpendicular to the axis as shown in FIG. 3(a), and is held by a retainer 13. In mounting the water/shavings-protection adaptor 2a to the transmission and conversion section 4, the adapter is connected through a seal packing 15 formed of rubber, silicone or the like to prevent cleaning water or tooth shavings from invading the transmission and conversion section 4.

Figure 3B:
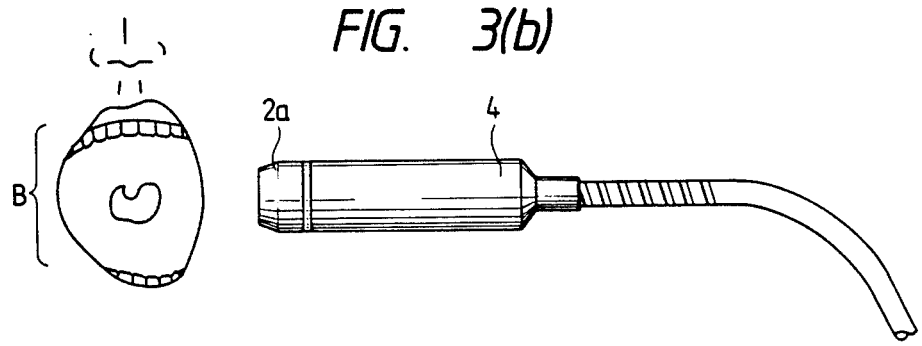

After mounting the water/shavings-protection adaptor 2a to the transmission and conversion section 4, to carry out observation of the inside of an oral cavity B, the transmission and conversion section 4 is inserted into the oral cavity B as shown in FIG. 3(b). Because the transmission and conversion section 4 includes three light guides 48, 48' for transmitting illumination light and the objective lens 43 for forming an image, the image can be detected by the image sensor 44 and, accordingly, displayed on, for example, the monitor television set 3a of the image processing section 3.

ENDOSCOPE

In the case of observing the inside of a root canal and cul-de-sac, it is necessary to use the image picking-up section having an insertion portion with a diameter less than that of a reamer for making a hole in a fang (root of tooth). Moreover, in the case of observing details of an oral cavity, it is necessary to insert the image picking-up section close to the object of observation in the oral cavity. Because the root canal and details of the oral cavity cannot be observed by the transmission and conversion section 4 itself, an endoscope 2b is mounted to the front end of the transmission and conversion section 4 to make such detailed observation possible. In the following, the endoscope 2b is described.

Figure 4A:
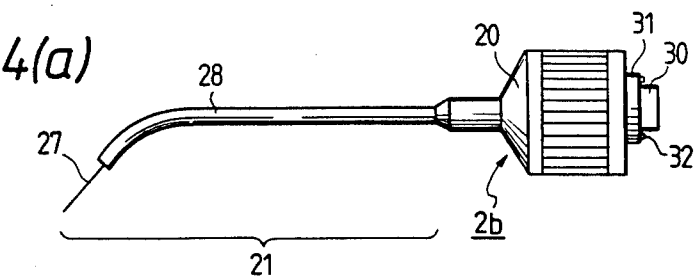
FIGS. 4(a) to 4(k) are views showing the specific structure of the endoscope depicted in FIG. 1.
Figure 4B:
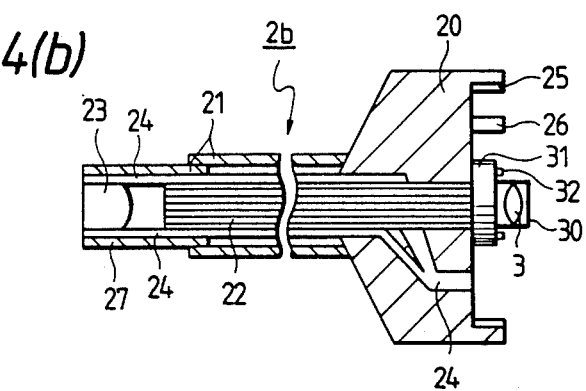
Figure 4C:
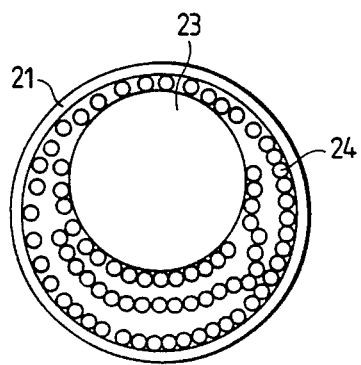

As shown in an appearance of FIG. 4(a) and a sectional view of FIG. 4(b), the external shape of the endoscope 2b is composed of a body 20 having a conical side, and a protection pipe 21 extended from an end of the body 20. An image fiber (bundle) 22 is disposed through the body 20 and the protection pipe 21 along the axis. An objective lens 23 for forming an image of a root canal is embedded in a tip portion of the protection pipe 21 so as to be disposed in front of an end surface of the image fiber 22. The image fiber 22 transmits the image formed by the objective lens 23. FIG. 4(c) shows a front end portion of the endoscope 2b. As shown in FIG. 4(c), a light guide 24 (optical fiber bundle) is arranged such that its end surface surrounds the objective lens 23 to make it possible to surely illuminate the object of observation.

The light guide 24 formed of an optical fiber bundle or the like is disposed through the body 20 and the protection pipe 21. The light guide 24 is branched into an upper portion and a lower portion within the body 20. On the other hand, within the protection pipe 21, the light guide 24 is disposed so as to surround the objective lens 23. The light guide 24 is connected to the light source 5b through the light guide 48 of the transmission and conversion section 4, so that the light guide 24 transmits light from the light source 5b and emits the light from its end to illuminate the object. In the rear end portion of the body 20, there are provided a female screw 25 for connecting the body 20 to the transmission and conversion portion 4 and at least two positioning pines 26 for positioning the body 20 against the transmission and conversion section 4.

As shown in FIG. 4(b), a guide lens 3, which is part of the lens system to form an image on the image sensor 44 of the transmission and conversion section 4, is mounted to the rear end portion of the body 20 of the endoscope 2b. The guide lens 3 is embedded in a cylindrical lens holder 30 which is threadedly engaged with a disc-shaped adjustment knob 31. The adjustment knob 31 is fixed to the body 20 with mounting screws 32. Thus the guide lens 3 is mounted to the body 20. The guide lens 3 acts to guide the image transmitted from the image fiber 22 of the endoscope 2b to the objective lens 43 of the transmission and conversion section 4. Accordingly, the guide lens 3 is mounted so as to be placed on the same optical axis as the image fiber 22 of the endoscope 2b. Alternatively, as described below, an adjusting knob may be unified with the body 20.

Figure 4D:
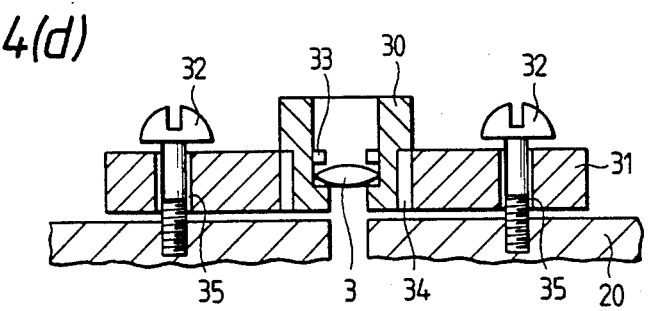
Figure 4E:
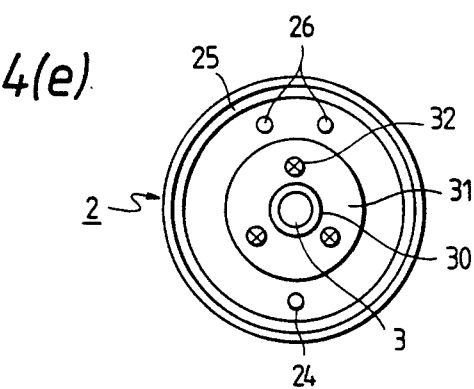
Figure 4F:
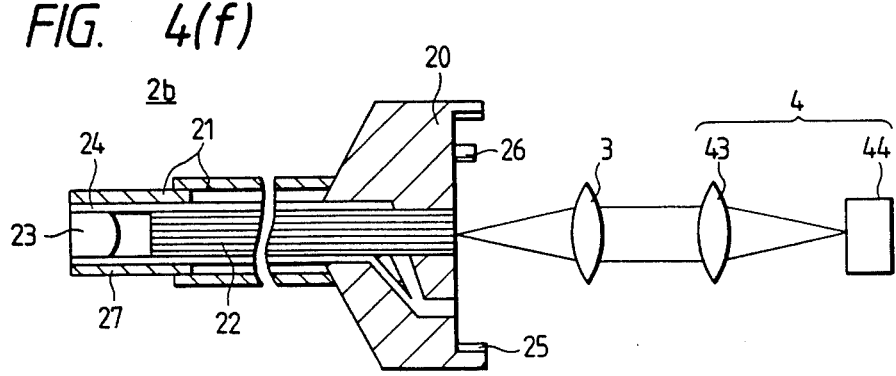
Figure 4G:
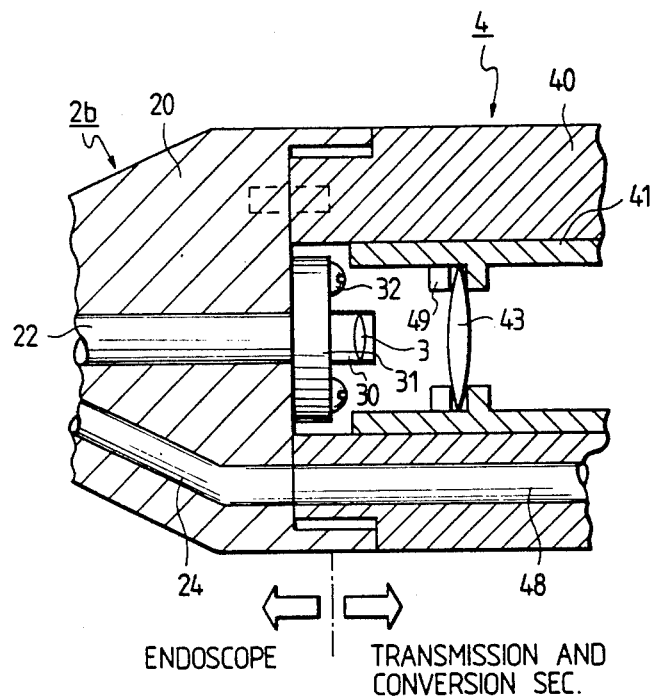
Figure 4H:
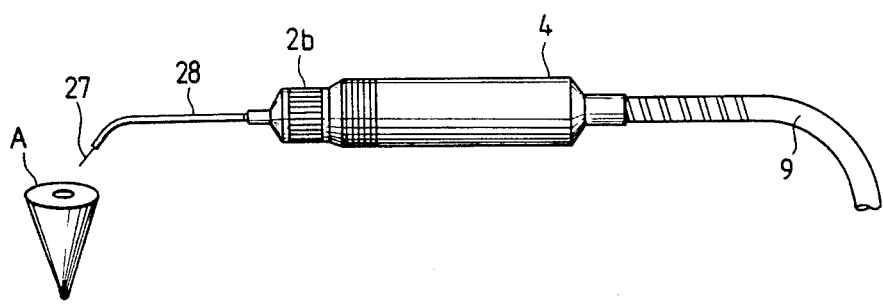
Figure 4I:
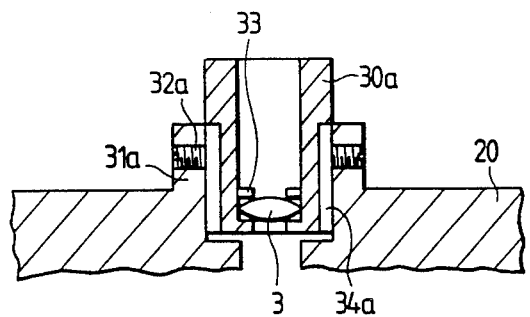
Figure 4J:
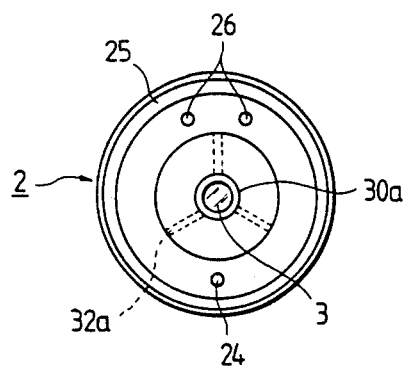

FIGS. 4(d) and 4(i) show structures for mounting the guide lens 3. FIGS. 4(e) and 4(j) show connection sides of the endoscope 2b to the transmission and conversion section 4.

As shown in FIGS. 4(d) and 4(e), in the first structure, the guide lens 3 is fixed within the lens holder 30 by a lens presser 33. The lens holder 30 and the adjustment knob 31 are threadedly engaged with each other at a thread portion 34. Further, the adjustment knob 31 is provided with adjustment holes 35 with a diameter larger than that of the mounting screws 32 so that the mounting screws 32 can be loosely inserted into the adjustment holed 35. With this structure, the guide lens 3 can be fixed to the body 20 through fixing the adjustment knob 31 to the body 20 with the mounting screws 32. On the contrary, by loosening the mounting screws 32, the adjustment knob 31 becomes movable along the rear end surface of the body 20. Accordingly, by moving the adjustment knob 31, the optical axis of the guide lens 3 can be made to coincide with that of the objective lens 43. Further, the lens holder 30 can be rotated with respect to the adjustment knob 31 which is fixed to the body 20. Because the rotation of the lens holder 30 produces a back-and-forth movement of the guide lens 3 along the optical axis, the focal length of the lens system can be adjusted.

As shown in FIGS. 4(i) and 4(j), in the second structure, an adjustment knob is unified with the body 20. The lens holder 30a and the rear end (adjustment knob 31a) of the body 20 are threadedly engaged with each other at the thread portion 34a. The lens holder 30a is fixed to the body 20 with fixing screws 32a from lateral directions. The thread portion 34a has been worked relatively loose so that the lens holder 30a becomes somewhat movable along the rear end surface of the body 20. The optical axis adjustment between the guide lens 3 and the objective lens 43 can be performed by properly moving the lens holder 30a through the manipulation of the fixing screws 32a.

FIG. 4(f) is a sectional view showing the basic structure of the optical system when the endoscope 2b is mounted to the transmission and conversion section 4. When the endoscope 2b for observation of the inside of a root canal is attached to the transmission and conversion section 4, the optical axis of the guide lens 3 provided in the rear (right) side of the endoscope 2b coincides with the optical axis of the optical system of the transmission and conversion section 4. The image appearing at the end surface of the image fiber 22 is focused on the image sensor 44 with the guide lens 3 of the endoscope 2b and the objective lens 43 of the transmission and conversion section 4.

Figure 4K:
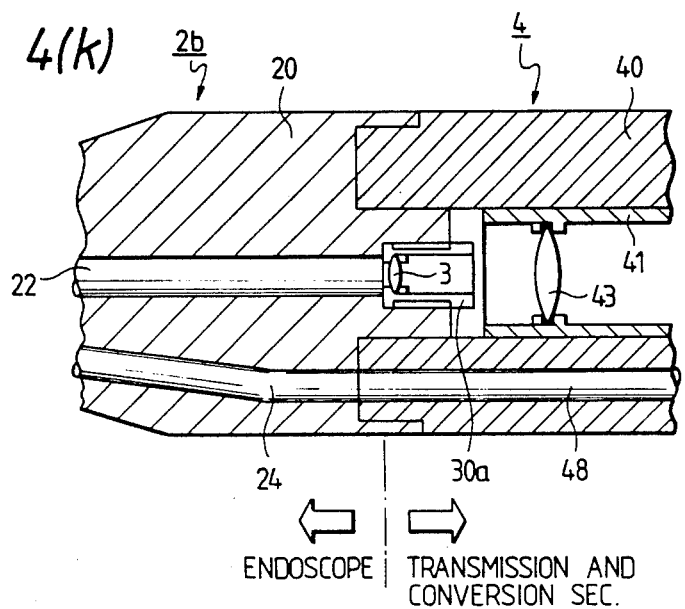

FIGS. 4(g) and 4(k) are sectional views showing the connection between the endoscope 2b and the transmission and conversion section 4.

As shown in FIG. 4(g), in the first structure, the guide lens 3 (fixed within the lens holder 30) is placed between the image fiber 22 of the endoscope 2b and the objective lens 43 of the transmission portion 4. When the endoscope 2b is attached to the transmission and conversion section 4, the optical axis of the guide lens 3 is adjusted to coincide with the optical axis of the objective lens 43 by sliding the adjustment knob 31 and, at the same time, the focal length of the lens system is adjusted by rotating the lens holder 30 with respect to the adjustment knob 31.

As shown in FIG. 4(k), in the second structure, the focal length of the lens system is adjusted by rotating the lens holder 30a with respect to the body 20. Furthermore, as described above, the optical axis adjustment of the lens system is performed using the fixing screws 32a and thereby the lens holder 30a is fixed to the body 20.

With these structures, the image formed by the objective lens 23 of the endoscope 2b and transmitted by the image fiber 22 is passed through the guide lens 3 and the objective lens 43 and then detected by the image sensor 44, so that the image can be displayed on, for example, the monitor television set 3a.

As shown in FIG. 4(g), the light guide 24 of the endoscope 2a is optically coupled to the light guide 48 of the transmission and conversion section 4, so that a series of light guides 24 and 48 pass through a series of bodies 20 and 40. The light guides 24 and 48 may be coupled at a junction plane between the bodies 20 and 40 or may be connected to each other with one end of the guides 24 and 48 being a projection and the other end being a dent. The leakage of light can be blocked more perfectly by applying an anti-reflection coating treatment to both the rear end source of the body 20 and the front end surface of the body 40, though the aforementioned structures themselves are effective for blocking the leakage of light from the junction between the bodies 20 and 40.

In the case of observation of the inside of an oral cavity, the front end of the light guide 48 of the transmission portion 4 acts as a light emitting end for illuminating the inside of the oral cavity. Further, a pair of light guides 48' are provided independent of the light guide 48 in the transmission and conversion section 4, as shown in FIG. 2(c). Accordingly, the pair of light guides 48' as well as the light guide 48 contribute to the illumination of the inside of the oral cavity, so that sufficient illumination intensity can be obtained.

In the meantime, for observation of the inside a root canal, the size of the insertion portion of the endoscope must be adapted to be not more than 1 mm.

Therefore, there is employed as shown in FIG. 4(a) such a structure that a diagnostic probe 28 covered with the protection pipe 21 is formed at the front portion of the endoscope 2b, and a tip 27 of the diagnostic probe 28 is inserted into the root canal (FIG. 4(h)). There prepared are a plurality of diagnostic probes 28 having respective bending angles to meet various parts for observation. Also prepared are a plurality of optical systems (objective lens, image fiber, etc.) and external structures to meet view ranges, etc. which are required corresponding to purposes of observation. Such external structures and optical systems of the endoscope will be described with reference to FIGS. 5 through 10.

Figure 5:
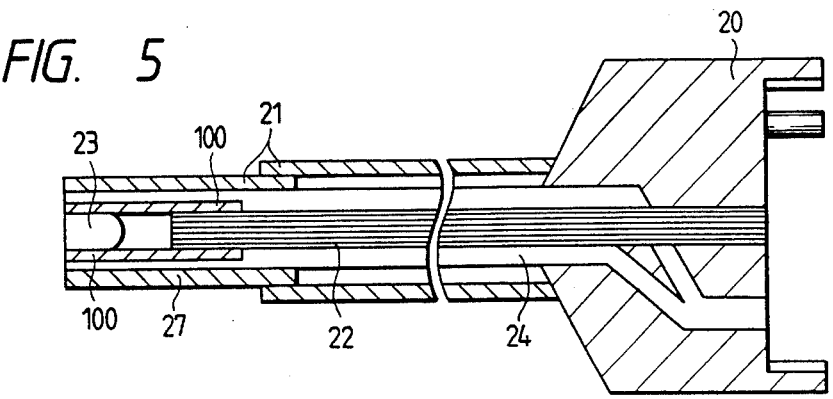
FIGS. 5 to 10 are views showing modifications of the endoscope.

As shown in FIG. 5, a connection pipe 100 may be provided in the endoscope 2b. The connection pipe 100 acts to prevent the positional shift between the objective lens 23 and the image fiber 22 which might be caused by collision with a hard tooth when the protection pipe 21 is inserted into a root canal. By means of the connection pipe 100, the image fiber 22 and the objective lens 23 can be fixed in the protection pipe 21 without axial displacement therebetween.

Figure 6A:
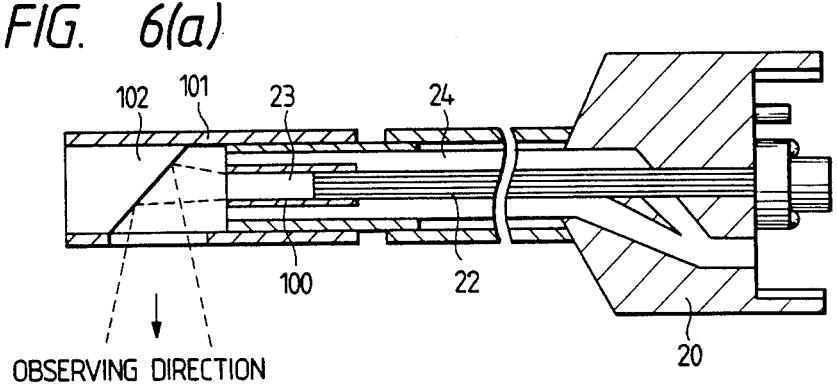

As shown in FIG. 6(a), a 90°-reflection mirror or rectangular prism 102 may be provided in a fixture pipe 101 mounted to the protection pipe 21. A downward observation direction can be obtained with this arrangement. However, in this case, since the reflection occurs just once, the obtained image of the object becomes a mirror-reversed one, which may be a problem in conducting a dental diagnosis. This problem can be solved by employing an arrangement necessitating two times of reflection. A roof-shaped prism may be used for this purpose.

Figure 6B:
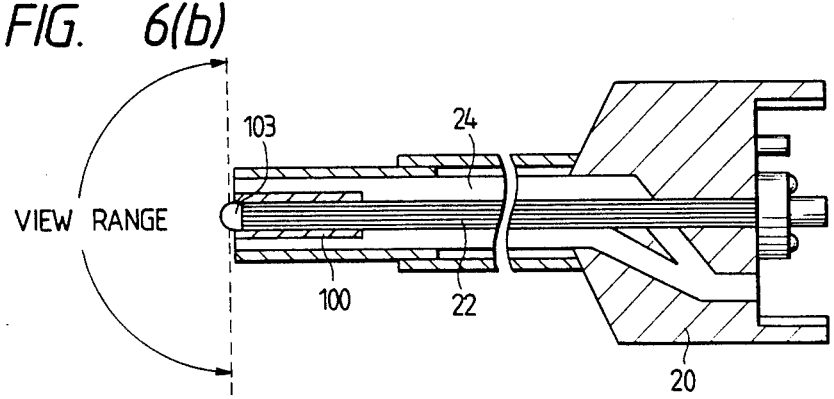

On the other hand, as shown in FIG. 6(b), a fisheye lens 103 may be embedded in the connection pipe 100 provided around the front end portion of the image fiber 22. In this case, a wide view range of about 180° can be obtained.

Figure 7A:
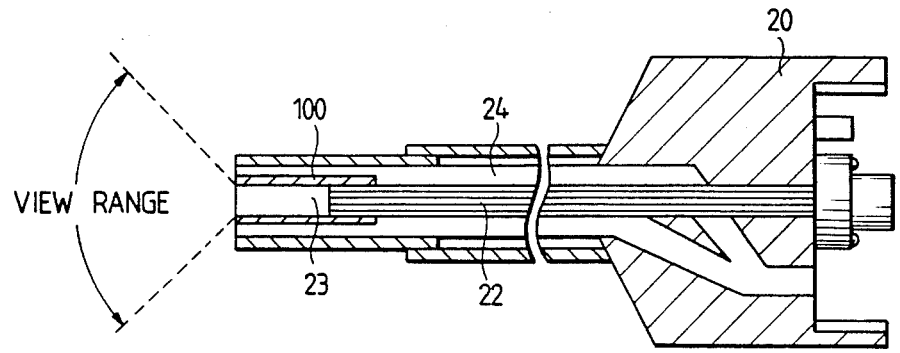
Figure 7B:
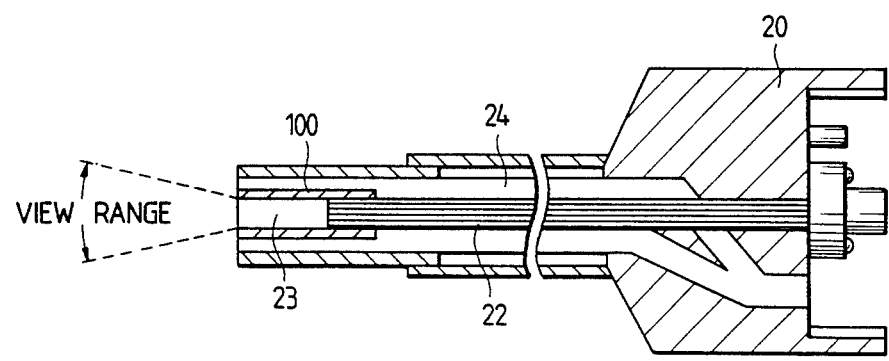

As shown in FIGS. 7(a) and 7(b), objective lenses 23 different in the view angle may be provided to obtain various view ranges. FIG. 7(a) shows the case where the view angle of the objective lens 23 is widened. FIG. 7(b) shows the case where the view angle of the objective lens 23 is narrowed.

Figure 8A:
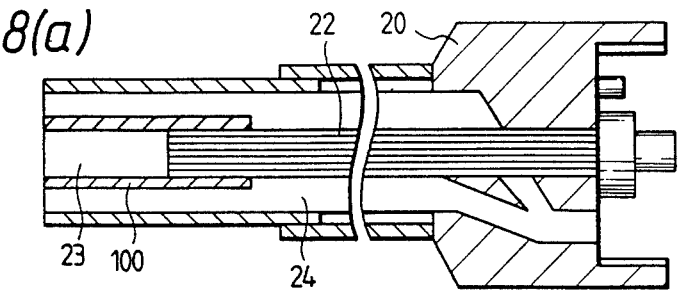

On the other hand, in the case of using a large-diameter image fiber 22 having a large number of picture elements or a large-diameter objective lens 23, the diameter of the protection pipe 21 may be enlarged as shown in FIG. 8(a). In this case, even a portion of the inside of the oral cavity which cannot be observed only by use of the transmission and conversion section 4 can be observed.

Figure 8B:
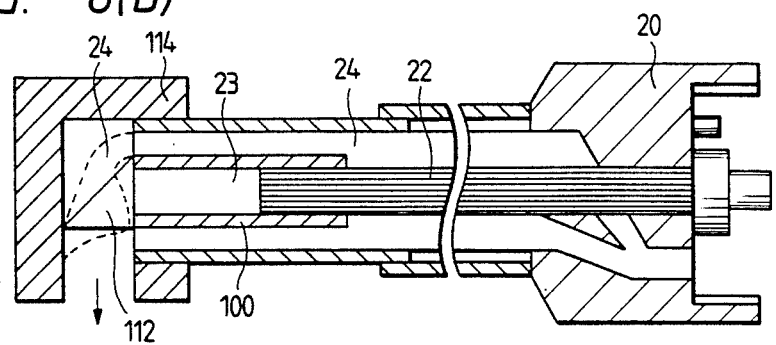
Figure 8C:
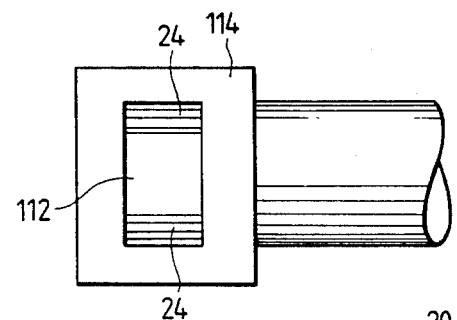
Figure 8D:
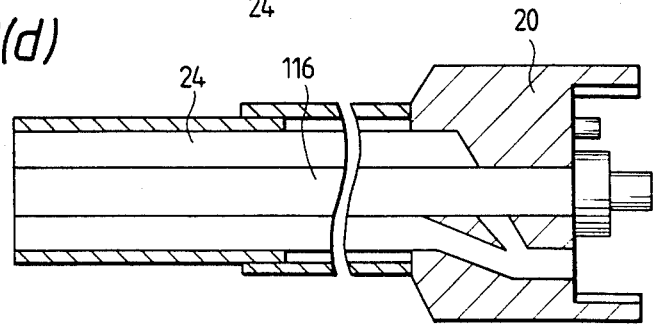

In the above case of the enlarged protection pipe 21, observation in the direction perpendicular to the optical axis, i.e. side observation, can also become possible by disposing a 90°-reflection mirror or prism 112 in front of the objective lens 23 as shown in FIGS. 8(b) and 8(c) (bottom view). The 90°-reflection mirror or prism 112 is embedded in a head cover 114 which is attached to the front end of the protection pipe 21. In order to supply the illumination light to the object the light guide 24 is protruded from the pipe 21 and bent to the observing direction. The head cover 114 is not only for protecting the mirror or prism 112 and the light guide 24, but also for preventing the oral cavity from being damaged. As shown in FIG. 8(d), the large-diameter image fiber 22 may be replaced by a rod lens 116.

Figure 9A:
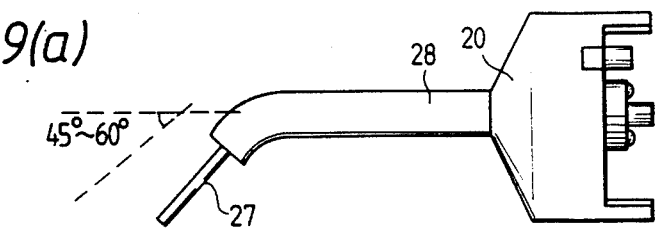
Figure 9B:
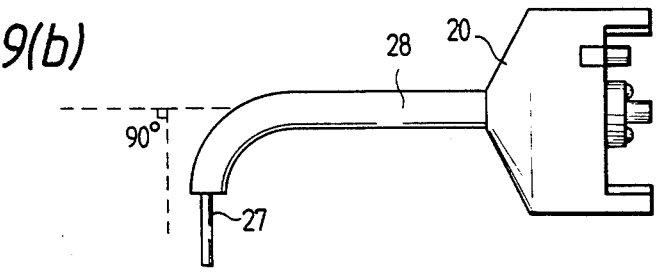

FIG. 9 shows examples in which the shape of the diagnostic probe 28 is changed. FIG. 9(a) shows the case where the diagnostic probe 28 is bent by an angle of about 45° to 60°. FIG. 9(b) shows the case where the diagnostic probe 28 is bent by an angle of about 90°. In the case of FIG. 9(a), the diagnostic probe 28 bent by a relatively small angle can be used for observation of periodontal portions and the inside of root canals. In the case of FIG. 9(b), the diagnostic probe 28 bent by a large angle can be used for observation of the back side of teeth, back teeth and the inside of root canals.

Figure 10A:
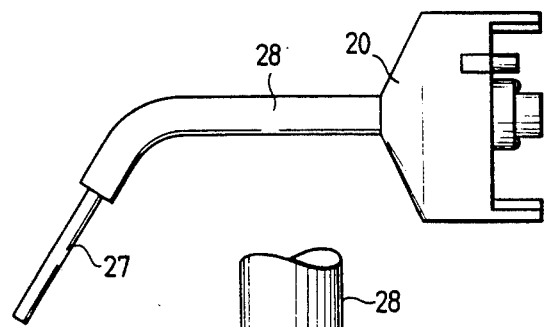
Figure 10B:
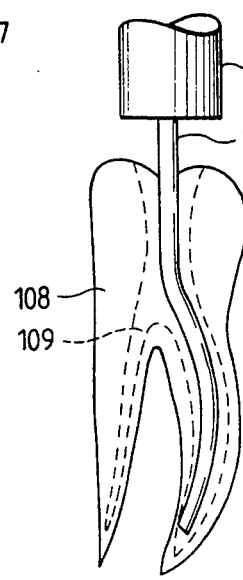

The tip 27 of the diagnostic probe 28 may be flexible as shown in FIGS. 10(a) and 10(b). In FIG. 10(a), an outer cover of the tip 27 is formed of a flexible material such as a Teflon tube, a Nylon tube or the like. The flexible tip 27 is inserted into a curved root canal 109 of a tooth 108 as shown in FIG. 10(b).

ZOOMING MECHANISM ADAPTOR

In observing the inside of an oral cavity with the transmission and conversion section 4 in which only the objective lens 43 acts as a lens system, the view range and magnification are limited. It is, however, necessary to change the view range and magnification to observe the inside of an oral cavity well. Therefore, it is preferable to attach an adaptor having a zooming mechanism.

Figure 11A:
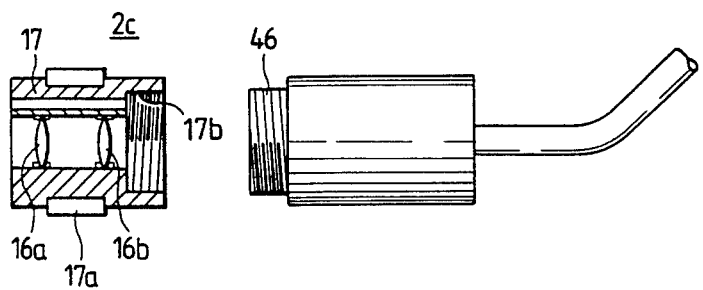
FIGS. 11(a) and 11(b) are views showing the structure of the zooming mechanism adaptor depicted in FIG. 1.
Figure 11B:
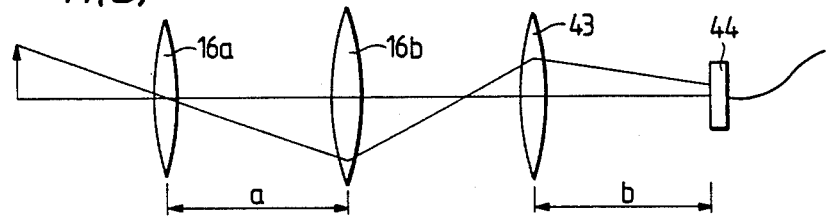

FIG. 11(a) shows a structure of a zooming mechanism adaptor 2c which can be attached to the transmission and conversion section 4. As shown in the drawing, the zooming mechanism adaptor 2c is composed of two lenses 16a and 16b, a holder 17 for holding the two lenses, and a focus/zoom ring 17a for operating a link mechanism (not shown) for moving the two lenses 16a and 16b in the axial direction while producing a predetermined relation between the two lenses 16a and 16b. A female screw 17b to be engaged with the male screw 46 of the transmission and conversion section 4 is formed in the connection side of the holder 17 to the transmission and conversion section 4. The optical axes of the lenses 16a and 16b are established to coincide with the optical axis of the objective lens 43 of the transmission and conversion section 4. Since the zooming mechanism used herein is the same as that of a zoom lens generally used in a camera, detailed description thereof will be omitted. A combination of the optical system of the zooming mechanism adaptor 2c and the optical system of the transmission and conversion section 4 is shown in FIG. 11(b). In FIG. 11(b), the distance b is constant. Accordingly, a wide-image can be obtained as the distance a increases. On the contrary, a tele-image can be obtained as the distance a decreases. The distance a can be changed by turning the focus/zoom ring 17a by hand. Alternatively, the distance a between the lenses 16a and 16b may be changed by operating the foot switch 6 connected to the control section 5 so as to energize an ultrasonic motor or the like. The mechanism of the water/shavings-protection adaptor 2a as explained above may by incorporated in the zooming mechanism adaptor 17 to prevent water and tooth shavings from invading the inside of the adaptor 17.

FILM ADAPTOR

In the dental treatment and the like, it is sometimes the case to take an X-ray photograph of a fang (root of tooth) to examine the condition of the fang with a transmission arrangement, or a photograph of an oral cavity to examine the degree of its recovery. In these cases, it is required that such image information is recorded and compared with other information.

To satisfy this requirement, the image information on a film must be converted into electronic information to facilitate search of the image information.

Figure 12A:
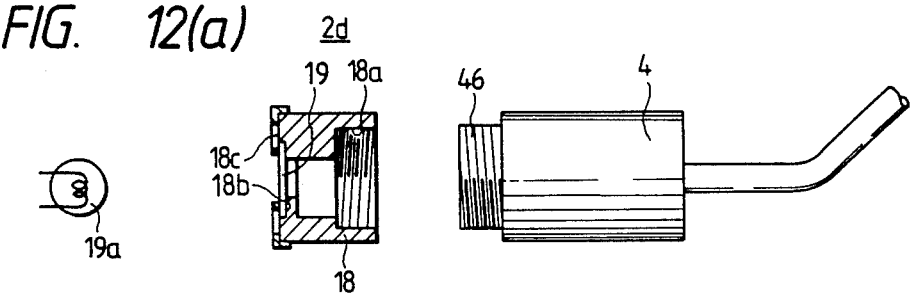
FIGS. 12(a) and 12(b) are views showing the structure of the film adaptor depicted in FIG. 1.
Figure 12B:
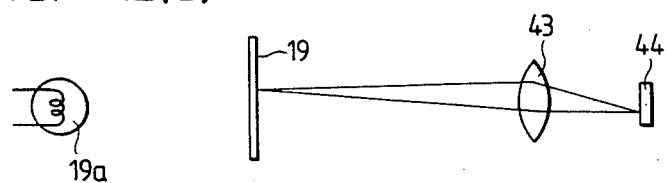

A structure of a film adaptor 2d attached to the transmission and conversion section 4 to pickup the image information on a film is shown in FIG. 12(a). As shown in the drawing, the film adaptor 2d has a substantially cylindrical adaptor body 18. A female screw 18a to be engaged with the male screw 46 of the transmission and conversion section 4 is formed in the inner surface of the connection side of the adaptor body 18 to the transmission and conversion section 4. Further, a retainer surface 18b for retaining a film 19 so as to keep the film surface perpendicular to the optical axis is formed on the adaptor body 18. The film 19 is pressed to the surface 18b and fixed to the adaptor body 18 by a fixing member 18c. Further, the adaptor body 18 has a through portion in its inside, so that the image information on the film surface can be focused on the image sensor 44 by the objective lens 43 in the presence of an external illumination light source (back light) 19a. When the film adaptor 2d is attached, the light source 5b is turned off so that the film 19 can be illuminated singly by the back light 19a. The optical system consisting of the film adaptor 2d and the transmission and conversion section 4 is shown in FIG. 12(b). As shown in FIG. 12(b), the film 19 is fixed in such a position that the image on the film 19 can be focused on the image sensor 44 by the objective lens 43 when the film 19 is illuminated by the external illumination light source 19a.

By using the film adaptor 2d, the image information on the film is easily picked up and transferred to the image processing section 3, so that realtime monitoring of an observed image can be made by the monitor television set 3a, etc.

IMAGE PROCESSING SECTION

As shown in FIG. 1, examples of the image processing section 3 include a monitor television set 3a, a VTR 3b, a still video recorder 3c, a video printer 3d, and a multivision display 3e. These image processing units are interchangeably connected to the control section 5, so that appropriate one is selected from these units according to the purpose of observation. For example, the VTR 3b can continuously record image information of an oral cavity. Since the still video recorder 3c can record image information of about 10 still-image scenes in one floppy disc, it is useful in searching. Further, the still video recorder 3c can be used for producing "video case history sheets". Since the video printer 3d can be used for generating a hard copy of image information, it is useful in dentist's making case history sheets. The multivision display 3e can be used for displaying a plurality of image information at once on a monitor television set. Accordingly, the multivision display 3e is useful for checking the course of dental treatment and for explaining it to a patient. Use of the multivision display unit 3e can facilitate data collection and arrangement of recorded information for each patient. By use of these image processing units in combination, better communication between a patient and dentist can be attained through the video information processing, thereby obtaining better curative results.

It is to be understood that the present invention is not limited to the aforementioned embodiments and that various changes may be made.

Although the embodiments have shown the case where the apparatus is applied to the dental treatment, it is a matter of course that the invention is not limited to the specific embodiments. For example, the invention can be generally applied to the case of dealing with image information or various objects of observation.

Although examples of the image picking-up section and examples of the image processing section have been described, it is a matter of course that the invention is not limited to the specific embodiments and that other devices or units may be used.

Although the embodiments have shown the case where three light guides are used in the transmission and conversion section 4, it is a matter of course that the invention is not limited to the specific embodiments and that the number of light guides is determined suitably. It is, however, preferable that two or more light guides are provided.

Figure 13A:
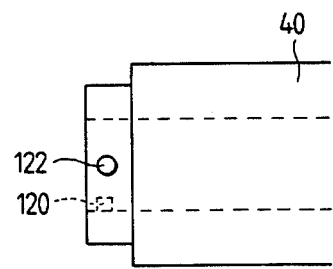
FIGS. 13 and 14 are views showing the modified structure for connecting the endoscope and transmission and conversion section.
Figure 13B:
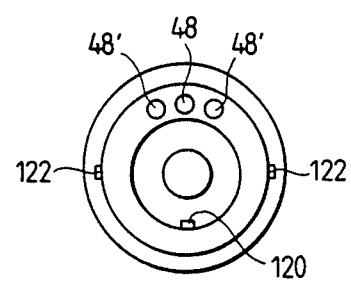
Figure 14A:
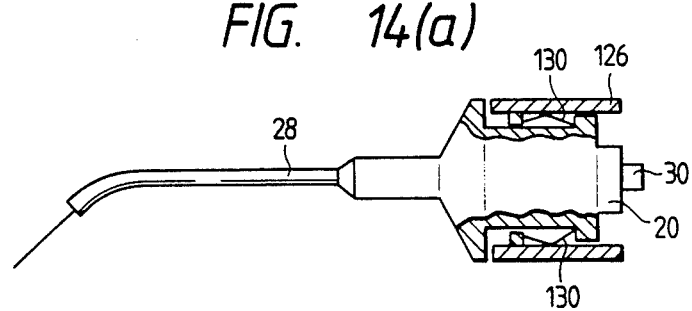
Figure 14B:
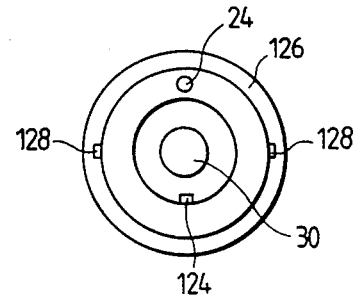

Although the detachable connection between the image picking-up section 2 (water/shavings-protection adaptor, endoscope, zooming mechanism adaptor, film adaptor, etc.) and the transmission and control section 4 has been described as the threaded engagement, it may be a connection structure employing springs and pins. This structure is explained for the case of the endoscope with reference to FIGS. 13 and 14. FIGS. 13(a) and 13(b) show a front view and side view of the transmission and conversion section 4, respectively. There are provided at the front end portion of the body 40 a positioning pin 120 for determining the relative arrangement of the bodies 20 and 40 in the connecting operation, and connection pins 122. FIGS. 14(a) and 14(b) show a front view (partially sectional) and side view of the endoscope 2b, respectively. As shown in FIG. 14(b), there are provided at the rear end portion of the body 20 a positioning groove 124 for receiving the positioning pin 120 and connection grooves 128 formed in a connection nut 126 for receiving the respective connection pins 122. As shown in FIG. 14(a), springs 130 are incorporated between the body 20 and the connection nut 126. The connecting operation is performed as follows. First, the body 20 is fitted to the body 40 so that the positioning groove 124 and positioning pin 120 are fitted to each other. Then, the connection nut 126 is rotated until the connection grooves 128 reach the positions corresponding to the respective connection pins 122. Finally, with being pulled to the transmission and conversion section 4 the connection nut 126 is rotated to complete the connection of the bodies 20 and 40. By further incorporating recesses in the connection grooves 128, into which the respective connection pins 122 are made fallen by means of the springs 130, the bodies 20 and 40 can be prevented from separating due to an accidental reverse rotation of the connection nut 126. This connection structure eliminates the need to incorporating pins in the body 20, i.e., in the adaptors of the image picking-up section 2. This means the reduction in the number of parts, because in the apparatus of the invention a plurality of adaptors of the image picking-up section 2 are interchangeably attached to one transmission and conversion section 4. Furthermore, there produced is an advantage that the "one-touch" connecting/separating operation of this structure is easier than that with the threaded engagement.

As described above in detail, according to the image processing apparatus of the present invention, various types of image information can be obtained by interchangeably attaching the various adaptors to the transmission and conversion section. Further, interchangeable processing units for processing the thus obtained image information are provided to reproduce required image information. Because various types of image information can be obtained by interchanging the adaptors, an image processing apparatus which is as a whole low in cost can be provided.

What is claimed is:

1. An image picking-up and processing apparatus, comprising:
    a transmission and conversion section comprising an image sensor for detecting input light which carries first image information of an object, a first objective lens for focusing said input light on said image sensor, and a first light guide for transmitting illumination light to illuminate said object, a front end portion of said transmission and conversion section having a structure enabling detachable connection to an interchangeable image picking-up section;
    a control section comprising a control unit for controlling said image sensor, and producing an image signal on the basis of an output signal from said image sensor, a light source for emitting said illumination light, and a second light guide for transmitting said illumination light from said light source to said first light guide; and
    an interchangeable image processing section for processing said image signal to reproduce second image information in a desired form, said image processing section being detachably connected to said control section.

2. An image picking-up and processing apparatus as claimed in claim 1, wherein said apparatus can detect said input light and reproduce said second image information without connecting said image picking-up section to said transmission and conversion section.

3. An image picking-up and processing apparatus as claimed in claim 1, further comprising as said image picking-up section a protection adaptor for protecting a mechanism inside said transmission and conversion section at least from water and tooth shavings which occur in a dental treatment.

4. An image picking-up and processing apparatus as claimed in claim 1, further comprising as said image picking-up section a film adaptor for holding a film such that an image of said film is focused on said image sensor when said film is illuminated by an external light source.

5. An image picking-up and processing apparatus as claimed in claim 1, further comprising as said image picking-up section a zooming mechanism adaptor including a lens system capable of performing zooming operation with respect to said object.

6. An image picking-up and processing apparatus as claimed in claim 1, wherein said transmission and conversion section further comprises a mechanism for moving said first objective lens along an optical axis thereof with respect to said image sensor.

7. An image picking-up and processing apparatus as claimed in claim 1, wherein said first light guide in said transmission and conversion section has a plurality of front ends to emit said illumination light.

8. An image picking-up and processing apparatus as claimed in claim 1, further comprising as said image picking-up section an endoscope for pickingup said first image information from an oral cavity or a root canal.

9. An image picking-up and processing apparatus as claimed in claim 8, wherein said endoscope comprises an image transmission member for transmitting said input light to said transmission and conversion section, a second objective lens for focusing an image of said object on a front end surface of said image transmission member, and a third light guide for transmitting said illumination light from said first light guide to illuminate said object.

10. An image picking-up and processing apparatus as claimed in claim 9, wherein said third light guide has a front end consisting of a bundle of optical fibers disposed so as to surround said second objective lens.

11. An image picking-up and processing apparatus as claimed in claim 9, wherein said image transmission member is an image fiber.

12. An image picking-up and processing apparatus as claimed in claim 9, wherein said image transmission member is a rod lens.

13. An image picking-up and processing apparatus as claimed in claim 9, wherein said endoscope further comprises an optical-path changing member disposed in front of said second objective lens for changing a traveling path of said input light reflected from said object, and said third light guide is protruded and bent to a direction consistent with said traveling path of said input light before incidence on said optical-path changing member.

14. An image picking-up and processing apparatus as claimed in claim 9, wherein said second objective lens is a fisheye lens.

15. An image picking-up and processing apparatus as claimed in claim 9, wherein a probe enclosing said image transmission member is bent by a specific angle from an optical axis of said endoscope.

16. An image picking-up and processing apparatus as claimed in claim 9, wherein a probe enclosing said image transmission member is flexible.

17. An image picking-up and processing apparatus as claimed in claim 9, wherein said endoscope further comprises a guide lens disposed in the rear of said image transmission member for focusing, in association with said first objective lens, said input light emitted from said image transmission member on said image sensor.

18. An image picking-up and processing apparatus as claimed in claim 17, wherein said endoscope further comprises a structure for holding said guide lens such that an optical axis of said guide lens can be adjusted so as to coincide with an optical axis of said first objective lens.

19. An image picking-up and processing apparatus as claimed in claim 9, wherein said endoscope further comprises an optical-path changing member disposed in front of said second objective lens for changing traveling paths of said illumination light and said input light reflected from said object.

20. An image picking-up and processing apparatus as claimed in claim 19, wherein said optical-path changing member changes said traveling paths two times.

* * * * *